US006607677B1

(12) United States Patent
Buchecker et al.

(10) Patent No.: US 6,607,677 B1
(45) Date of Patent: Aug. 19, 2003

(54) OPTICALLY ACTIVE COMPOUNDS

(75) Inventors: Richard Buchecker, Zürich (CH); Zoubair Mohammed Cherkaoui, Allschwil (CH); Klaus Schmitt, Lörrach (DE)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 09/719,333

(22) PCT Filed: Jun. 4, 1999

(86) PCT No.: PCT/IB99/01034

§ 371 (c)(1),
(2), (4) Date: Dec. 11, 2000

(87) PCT Pub. No.: WO99/64383

PCT Pub. Date: Dec. 16, 1999

(30) Foreign Application Priority Data

Jun. 12, 1998 (GB) ............................................. 9812800

(51) Int. Cl.⁷ .......................... C07C 33/26; C09K 19/58
(52) U.S. Cl. .................................. 252/299.01; 549/453
(58) Field of Search ....................... 252/299.01–299.7; 568/833; 428/694; 525/32.2; 524/513, 601; 549/453

(56) References Cited

U.S. PATENT DOCUMENTS 4,968,820 A    11/1990    Scherowsky et al.

FOREIGN PATENT DOCUMENTS

EP    0 233 602    8/1987
WO    WO 97/34886    9/1997

OTHER PUBLICATIONS

Wünsch et al,, "Diastereoselective Addition of Chiral (2–Lithiophenyl)acetaldehyde Acetals to Various Imines as Key Step in the Asymmetric Synthesis of 1–Aryltetrahydroisoquinolines, Part 4"; Eur. J. Org. Chem. Feb., 1999; vol. 11, Issue 2, pp. 503–517.*

Derwent Abstract of WO 97/34886.

Kuball et al. "174. TADDOLs with Unprecedented Helical Twisting Power in Liquid Crystals," Helvetica Chimica Acta, vol. 80, pp. 2507–2514 (1997).

Dube et al., "A Novel Bicyclic Orthoester as a Chiral Auxiliary: Application to the Synthesis of α–Hydroxy Acids," Tetrahedron Letters, vol. 36, pp. 1827–1830 (1995).

* cited by examiner

*Primary Examiner*—Mark F. Huff
*Assistant Examiner*—Jennifer R. Sadula
(74) *Attorney, Agent, or Firm*—Finnegan, Henderson, Farabow, Garrett & Dunner, LLP

(57) ABSTRACT

Optically active butane-1,2,3,4-tetraol derivatives of formula (I). The compounds may be used as doping agents for liquid crystals for a wide range of applications, such as solid state cholesteric filters for projection displays, circular polarizers, and optical filters.

23 Claims, No Drawings

OPTICALLY ACTIVE COMPOUNDS

This application is a national stage filing under 35 U.S.C. §371 of international application no. PCT/IB99/1034, filed on Jun. 4, 1999, which published in the English language.

This invention relates to optically active materials and their use as doping agents for liquid crystals for a wide range of applications including solid state cholesteric filters for projection displays, circular polariser, optical filter, etc.

The addition of an optically-active compound to a non-optically-active liquid crystalline phase is one of procedures used for the conversion of non-optically-active into optically-active mesophases. The nematic phase, for example, is converted to the cholesteric one when being doped with a small amount of an optically-active substance. This conversion manifests itself by the occurrence of an intermolecular helix which is characterised by the so-called helical twisting power (HTP) given in Equation 1:

$$HTP = \left|\frac{dp^{-1}}{dx}\right|_{x=0} \cong \frac{p^{-1}}{x} = \sum_i x_i (HTP), \quad (1)$$

Said HTP is in fact a measure for the efficiency of a given dopant and is determined by the Cano method with solutions of the dopant in the host mesophase. Since the optically-active guest and the non-optically-active host compounds are not necessarily compatible at the molecular scale, their binary solution is frequently characterised by undesirable changes of the thermo-tropic sequence of the initial host liquid crystalline material, like for example a depression of the clearing point. Those changes could in turn have negative effects on the phase properties of the host, such as a decrease of the birefringence etc. Therefore, an optically-active dopant is sought so that with very small concentrations of this latter, large values of HTP could be induced.

As such efficient optically-active dopants there are the binaphthol derivatives described in GB-A-2 298 202. However optically-active binaphthol derivatives may undergo partial racemisation when being heated. Besides, their preparation is expensive because it includes asymmetric resolution of binaphthol racemate as a crucial reaction step.

Another type of optically-active dopants are the TADDOLs derivatives (α,α,α',α'-tetraaryl-1,3-dioxolane-4,5-dimethanols). They have been known for 15 years in asymmetric syntheses (D. Seebach et al., *J. Org. Chem.* 60, 1788, (1995) and *Helv. Chim. Acta* 80, 2515, (1997)) and recently investigated as dopants in nematic host mesophases and found to induce large values of HTP (H. G. Kuball et al., *Helv. Chim. Acta* 80, 2507, (1997) and International Patent Application WO-A-97/34886). This efficiency of TADDOLs compounds was essentially attributed to their conformational stability due to the presence of the dioxolane ring.

*Tet. Lett.* 36(11), 1995, 1827–1830 (Dube et al.) discloses the compound (2R,3R)-1,1,4,4-tetraphenylbutane-1,2,3,4-tetraol as an intermediate in asymmetric synthesis:

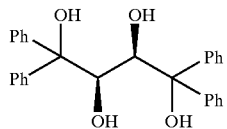

However, no activity is given for the compound.

EP-A-0233602 (Hoechst AG) relates to chiral dopants for liquid crystals. The compounds are all derivatives of butane-1,2,3,4-tetraol of general formula:

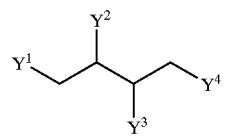

having no further substituents on the butane backbone.

It has been suggested that the large HTP observed with TADDOLs compounds is due to their conformational stability. However we have now discovered that further compounds that exhibit overcrowding of the chiral atoms and are sterically hindered at positions analogous to the α,α' positions in TADDOLs are equally effective at producing a large HTP.

Thus the invention provides optically active butane-1,2,3,4-tetraol derivatives of formula I:

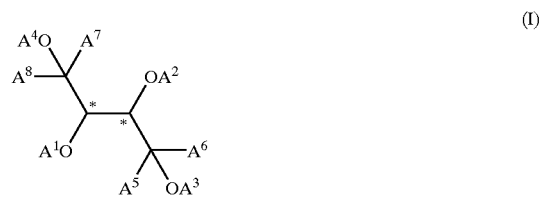

in which
$A^1$, $A^2$, $A^3$, $A^4$ each independently represents hydrogen; or an optionally-substituted methyl group; or an optionally-substituted aliphatic group with 2 to 80 C-atoms, in which one or more C-atoms may be replaced by a heteroatom or a group —SO—, —SO$_2$—, —SOO—, —OSO— or —SOS—; or an optionally-substituted aromatic or non-aromatic carbocyclic or heterocyclic ring system, with 1 to 80 C-atoms; and $A^5$, $A^6$, $A^7$, $A^8$ each independently represents an optionally-substituted aliphatic group with 3 to 80 C-atoms, in which a C-atom, or two or more non-adjacent C-atoms, may be replaced by a heteroatom or a group —SO—, —SO$_2$—, —SOO—, —OSO— or —SOS—; or an optionally-substituted aromatic or non-aromatic carbocyclic or heterocyclic ring system, with 1 to 80 C-atoms; or one, two or three of $A^5$, $A^6$, $A^7$ and $A^8$ independently represents hydrogen; or an optionally-substituted methyl group; or an optionally-substituted aliphatic group with 2 C-atoms, in which a C-atom may be replaced by a heteroatom; and the remainder of $A^5$, $A^6$, $A^7$, $A^8$ independently represent an optionally-substituted aliphatic group with 3 to 80 C-atoms, in which a C-atom, or two or more non-adjacent C-atoms, may be replaced by a heteroatom, or a group —SO—, —SO$_2$—, —SOO—, —OSO— or —SOS—; or an optionally-substituted aromatic or non-aromatic carbocyclic or heterocyclic ring system, with 1 to 80 C-atoms;

with the provisos that:
when one, two or three of $A^5$, $A^6$, $A^7$ and $A^8$ represents hydrogen, then $A^5$, $A^6$, $A^7$ and $A^8$ may not represent COOH; and
when $A^5$, $A^6$, $A^7$ and $A^8$ are all phenyl, then at least one of $A^1$, $A^2$, $A^3$, $A^4$ does not represent hydrogen.

The term "aliphatic" includes straight-chain and branched alkyl, as well as saturated and unsaturated groups. Possible substituents include alkyl, aryl (thus giving an araliphatic group) and cycloalkyl, as well as amino, cyano, epoxy, halogen, hydroxy, nitro, oxo etc. Possible heteroatoms which may replace carbon atoms include nitrogen, oxygen and sulphur. In the case of nitrogen further substitution is possible with groups such as alkyl, aryl and cycloalkyl.

In the case of the present invention, owing to the absence of the dioxolane ring, the new optically active butane-1,2,3,4-tetraol derivatives of formula I have obviously more conformational freedom then TADDOLs derivatives. However they were surprisingly found still to induce large values of HTP when being used as dopants in nematic host systems, as will be demonstrated in the forthcoming sections.

The compounds of the invention may be used as doping agents for liquid crystals for a wide range of applications including solid state cholesteric filters for projection displays, circular polarisers, optical filters, etc.

Although one or more of $A^5$, $A^6$, $A^7$ and $A^8$ may represent a small group such as hydrogen or an optionally-substituted methyl group, we prefer there to be two bulkier groups, $A^5$ and $A^6$, attached to the same carbon atom. Thus preferably only $A^7$ and $A^8$ may represent hydrogen. More preferably only one of $A^5$, $A^6$, $A^7$ and $A^8$ may represent hydrogen. The best compounds are those which have four bulky groups. Thus, preferably $A^5$, $A^6$, $A^7$ and $A^8$ each independently represents an optionally-substituted aliphatic group with 3 to 80 C-atoms, in which a C-atom, or two or more non-adjacent C-atoms, may be replaced by a heteroatom or a group —SO—, —SO$_2$—, —SOO—, —OSO— or —SOS—; or an optionally-substituted aromatic or non-aromatic carbocyclic or heterocyclic ring system, with 1 to 80 C-atoms. Carbocyclic or heterocyclic ring system having two or more fused rings have been found to be particularly suitable.

The invention further relates to optically active butane-1,2,3,4-tetraol derivatives of formula I, in which:

$A^1$, $A^2$, $A^3$, $A^4$ each independently represents hydrogen; or an optionally-substituted methyl group; or an optionally-substituted aliphatic group with 2 to 80 C-atoms, in which one or more C-atoms may be replaced by a heteroatom or a group —SO—, —SO$_2$—, —SOO—, —OSO— or —SOS—; or an optionally-substituted aromatic ring system, with 1 to 80 C-atoms; and $A^5$, $A^6$, $A^7$, $A^8$ each independently represents an optionally-substituted aliphatic group with 3 to 80 C-atoms, in which a C-atom, or two or more non-adjacent C-atoms, may be replaced by a heteroatom or a group —SO—, —SO$_2$—, —SOO—, —OSO— or —SOS—; or an optionally-substituted aromatic ring system, with 1 to 80 C-atoms; with the proviso that, when $A^5$, $A^6$, $A^7$ and $A^8$ are all phenyl, then at least one of $A^1$, $A^2$, $A^3$, $A^4$ does not represent hydrogen.

Particularly interesting applications are possible if at least one of the $A^1$ to $A^6$ residues includes a polymerisable group.

Preferred embodiments of the invention relates to optically active butane-1,2,3,4-tetraol derivatives of formula I, wherein:

$A^5$ to $A^8$ have each independently one of the meanings of formula II:

—X$^1$—(Sp$^1$)$_n$—X$^2$—(MG)—X$^3$—(Sp$^2$)$_m$—P (II)

$A^1$ to $A^4$ are hydrogen atoms or have each independently one of the meanings of formula IIb or one of the meanings of formula IIc:

—(Sp$^1$)$_n$—X$^2$—(MG)—X$^3$—(Sp$^2$)$_m$—P (IIb)

—(Sp$^1$)$_n$—X$^2$—(MG)—X$^4$ (IIc)

in which:

$X^1$ to $X^3$ each independently denote —O—, —S—, —NH—, —N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH—, —C≡C— or a single bond, in such a manner that oxygen atoms are not linked directly to one another;

$X^4$ is a halogen;

Sp$^1$ and Sp$^2$ are each independently straight or branched spacer groups having 1 to 20 C-atoms which may be unsubstituted, or mono- or polysubstituted by halogen or CN, it being also possible for one or more non-adjacent CH$_2$ groups to be replaced, in each case independently from one another, by —O—, —S—, —NH—, —N(CH$_3$)—, —CH(OH)—, —CO—, —CH$_2$(CO)—, —CH$_2$(SO)—, —CH$_2$(SO$_2$)—, —COO—, —OCO—, —OCO—O—, —S—CO—, —CO—S—, —C≡C—, —(CF$_2$)$_r$—, —(CD$_2$)$_s$— or —C(W$^1$)=C(W$^2$)—, r and s ranging between 1 and 15, and W$^1$ and W$^2$ each independently denoting H, H—(CH$_2$)$_q$— or Cl with q ranging between 1 and 15;

P is hydrogen or preferably a polymerisable group selected from the formulae CH$_2$=CW—, CH$_2$=CW—COO—, CH$_2$=C(Ph)—COO—, CH$_2$=CH—COO—Ph—, CH$_2$=CW—CO—NH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C=N—(CH$_2$)$_{m3}$, HO—, HS—, HO—(CH$_2$)$_{m3}$—, HS—(CH$_2$)$_{m3}$—, HO(CH$_2$)$_{m3}$COO—, HS(CH$_2$)$_{m3}$COO—, HWN—, HOC(O)—, CH2=CH—Ph—(O)$_{m4}$,

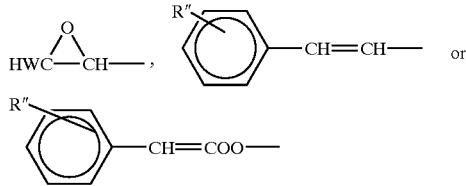

with W being H, Cl or alkyl with 1–5 C atoms, m3 being 1–9, m4 being 0 or 1, Ph being phenyl, R' being alkyl with 1–5 C atoms, and R" having the meaning or R' or being methoxy, cyano or a halogen;

n and m are each independently 0 or 1; and

MG denotes a mesogenic group comprising 1 to 4 aromatic or non-aromatic carbocyclic or heterocyclic ring systems and optionally up to 3 bridging groups, and preferred are those selected from the meanings of formula III:

C$^1$—(Z$^1$—C$^2$)$_{a1}$—(Z$^2$—C$^3$)$_{a2}$—(Z$^3$—C$^4$)$_{a3}$ (III), in which:

$C^1$ to $C^4$ are in each case independently optionally-substituted non-aromatic, aromatic, carbocyclic or heterocyclic groups;

$Z^2$ to $Z^3$ are independently from each other —COO—, —OCO—, —CH$_2$—CH$_2$—, —OCH$_2$—, —CH$_2$O—, —CH=CH—, —C≡C—, —CH=CH—COO—, —OCO—CH=CH— or a single bond; and a1, a2 and a3 are independently integers 0 to 3, such that a1+a2+a3≦4.

Especially preferred are those in which $C^1$ to $C^4$ are selected from:

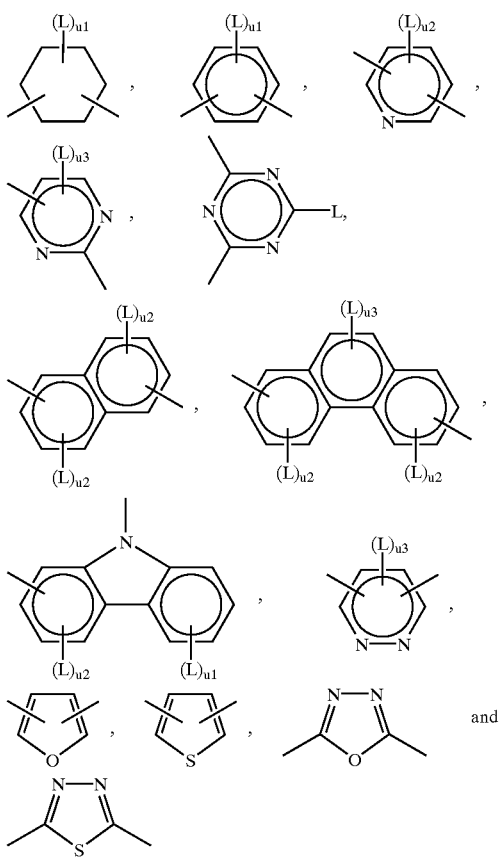

with:
L being —CH$_3$, —COCH$_3$, —NO$_2$, CN, or halogen,
u1 being 0, 1, 2, 3, or 4,
u2 being 0, 1, 2, or 3, and
u3 being 0, 1, or 2.

We have discovered that, to attain high values of HTP for a given guest-host liquid crystalline system, it is desirable to increase the size and the conformational stability of the substituents around the chiral centre(s) of the optionally active host molecule(s). It is possible to realise such a strategy in the present invention with optically active butane-1,2,3,4-tetraol derivatives of formula I where the two 1 and 4 positions could be derivatised with bulky A$^5$ to A$^9$ substituents starting, for example, from the Grignard analogues of A$^5$ to A$^8$ of appropriate structure, selected from the formula II and tartaric acid, commercially available in both (R,R) and (S,S) enantiomeric forms. The four generated hydroxy groups could be then derivatised, using classical synthetic methods, with A$^1$ to A$^4$ appropriately selected from the formula IIb as organic residues permitting the increase of solubility and/or the increase of compatibility of I with the guest liquid crystalline systems.

More preferred embodiments of the present invention are:
a) for ease of synthesis, optically active butane-1,2,3,4-tetraol derivatives of formula I wherein:
A$^1$ and A$^2$ are identical, and
A$^3$ and A$^4$ are identical, and
A$^5$ and A$^8$ are identical; and
b) optically active butane-1,2,3,4-tetraol derivatives of formula I wherein:

A$^3$ and A$^4$ have one of the meanings of formula IV:

A$^1$ and A$^2$ have one of the meanings of formula VA:

and
A$^5$ to A$^8$ have one of the meanings of formula VB:

in which:
Sp$^2$ is alkylene with 0 to 20 C-atoms,
P$^2$ is H, CH$_2$=CW$^5$— or CH$_2$=CW$^5$—CO—,
P$^3$ is H, CH$_2$=CW$^5$—, CH$_2$=CW$^5$—COO—, W$^5$CH=CH—O— or CH$_2$=CW$^5$—O—, with W$^5$ being H, CH$_3$, or Cl,
m$^4$ and m$^5$ are each independently 0 or 1 in such a manner that oxygen atoms are not linked directly to one another,
MG is selected from:

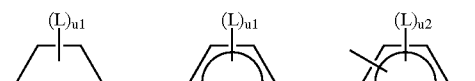

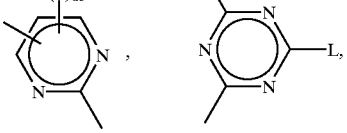

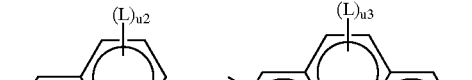

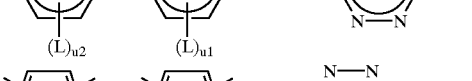

X$^3$ is —O—, —CO—, —COO—, —OCO—, —CH$_2$—CH$_2$—, —OCH$_2$—, —CH$_2$O—, —CH=CH—, —C≡C—, —CH=CH—COO—, —OCO—CH=CH— or a single bond, and
X$^5$ is —CO— or —CH$_2$—.

Preferred compounds of formula I are those for which A$^3$ and A$^4$ have one of the meanings of formula IV, A$^1$ and A$^2$ have one of the meanings of formula VA and A$^5$ to A$^8$ have one of the meanings of formula VB, in which:

MG is cyclohexylene, phenylene, biphenylene, naphthylene or phenanthrylene, $X^3$ denotes —O—, —CO—, —COO—, —OCO—, —C≡C—, or a single bond, in particular —O— or a single bond, $Sp^2$ is straight-chain of formula —$(CH_2)_v$—, with v being an integer between 0 and 20, especially preferred being ethylene, propylene, butylene, pentylene, hexylene, heptylene, octylene, nonylene, decylene, undecylene, or dodecylene, $P^2$ is H, $CH_2$=$CW^5$— or $CH_2$=$CW^5$—COO—, $P^3$ is H, $CH_2$=$CW^5$—, $CH_2$=$CW^5$—COO—, $W^5CH$=CH—O— or $CH_2$=$CW^5$—O—, with $W^5$ being H, $CH_3$, or Cl, and $m^4$ and $m^5$ are each independently 0 or 1 in such a manner that oxygen atoms are not linked directly to one another.

Other aspects of the present invention are:

a) a liquid crystalline material, especially in the form of a liquid crystalline mixture, (co)polymer, elastomer, polymer gel or polymer network, comprising at least two components, at least one of which is an optically active compound, characterised in that the optically active compound is a butane-1,2,3,4-tetraol derivative of formula I;

b) a liquid crystalline material, especially in the form of a cholesteric mixture, or cholesteric polymer network, comprising at least two components, at least one of which is an optically active compound, characterised in that the optically active compound is a butane-1,2,3,4-tetraol derivative of formula I;

c) a cholesteric polymer network obtainable by copolymerisation of an optically active polymerisable mesogenic mixture comprising:
  i) at least one optically-active or/and non-optically-active nematic polymerisable compound which can be chosen from the already reported broad range of optically-active and non-optically-active nematic materials, for example in *Adv. Mater.* 5, 107 (1993), *Mol. Cryst. Liq. Cryst.* 307, 111 (1997), *J. Mat. Chem.* 5, 2047 (1995) or in patent applications U.S. Pat. Nos. 5,593,617 and 5,567,349; GB-A-2 297 556; GB-A-2 299 333; DE-A-19 504 224; EP-A-0 606 940; EP-A-0 643 121 and EP-A-0 606 939; optionally selected from EP-A-0 606 940, EP-A-0 643 121 and EP-A-0 606 939,
  ii) at least one optically active dopant of formula I,
  iii) an initiator,
  iv) optionally a non-mesogenic compound having at least one polymerisable functional group, more optionally a diacrylate compound, and
  v) optionally a stabiliser;

d) optically-active polymerisable cholesteric mixtures, essentially consisting of:
  i) 70 to 99%, preferably 85 to 95% by weight of at least one non-optically-active polymerisable liquid crystal,
  ii) 0.1 to 30%, preferably 1 to 15% by weight of an optically active compound of formula I,
  iii) 0.1 to 5%, preferably 0.2 to 2% by weight of a photoinitiator,
  iv) 0 to 5%, preferably 0.1 to 1% of a stabiliser, and e) a cholesteric film obtainable by the steps comprising ordering the above mixture in the monomeric state and in situ UV polymerisation of the resulting ordered mixture.

The inventive optically active compounds disclosed in the foregoing and the following can be prepared by methods which are known per se and which are described in standard works of organic chemistry such as, for example, Houben-Weyl, *Methoden der Organischen Chemie,* Thieme-Verlag, Stuttgart. In the present case of compounds I the commercially available (R,R)- and (S,S)-dimethyl tartrate are used as starting materials, for example according to the following reaction schemes:

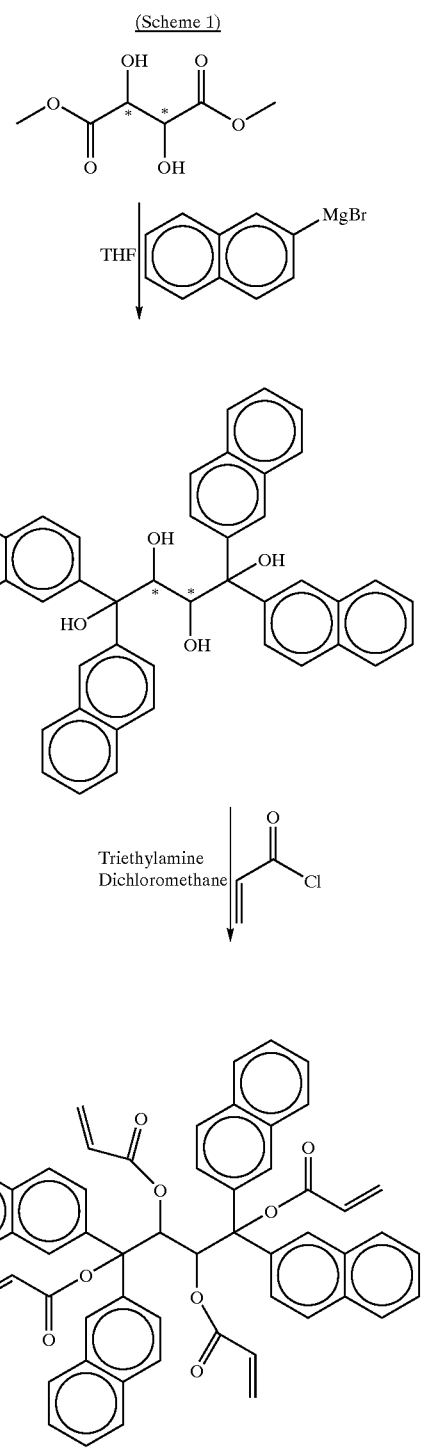

(Scheme 2)
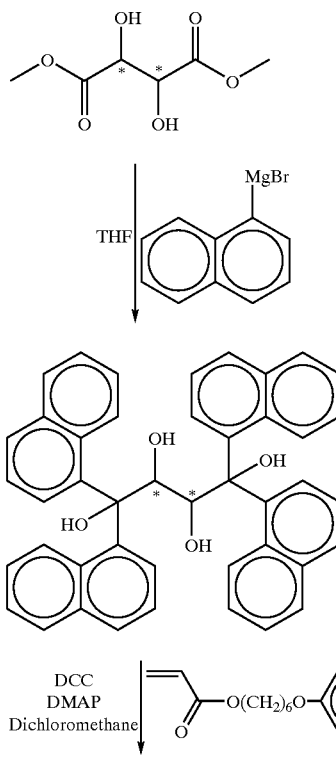
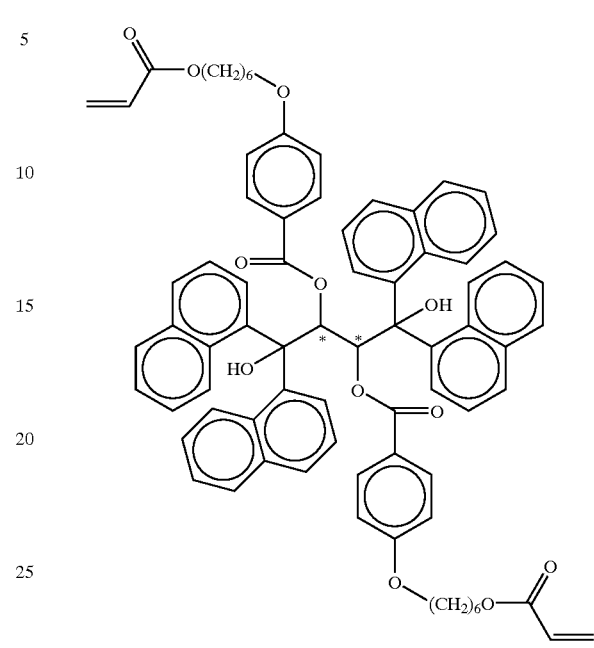
(Scheme 3)
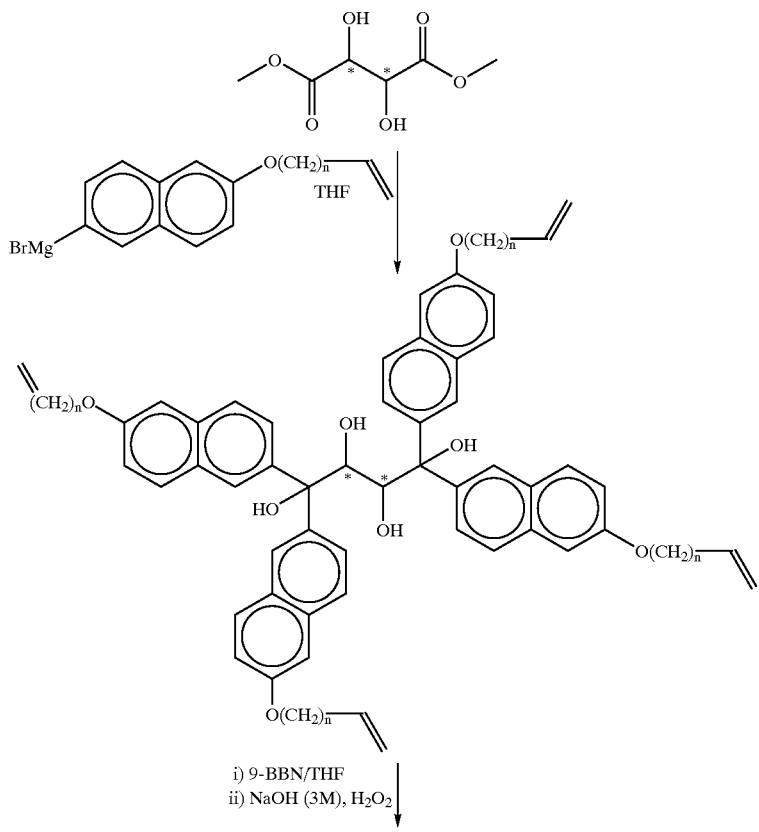
i) 9-BBN/THF
ii) NaOH (3M), H$_2$O$_2$

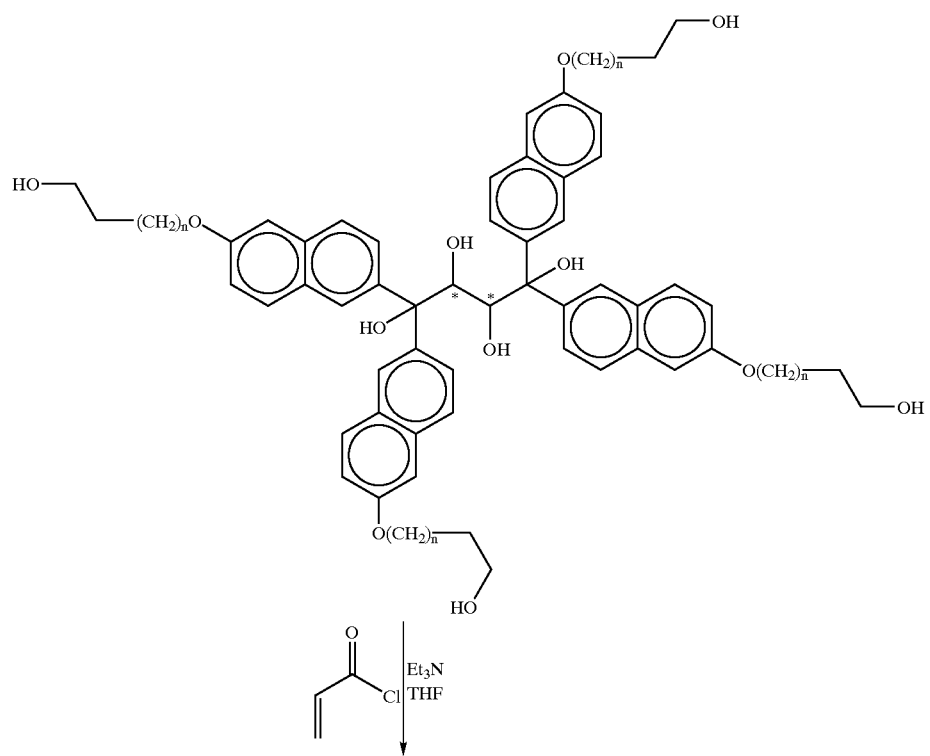
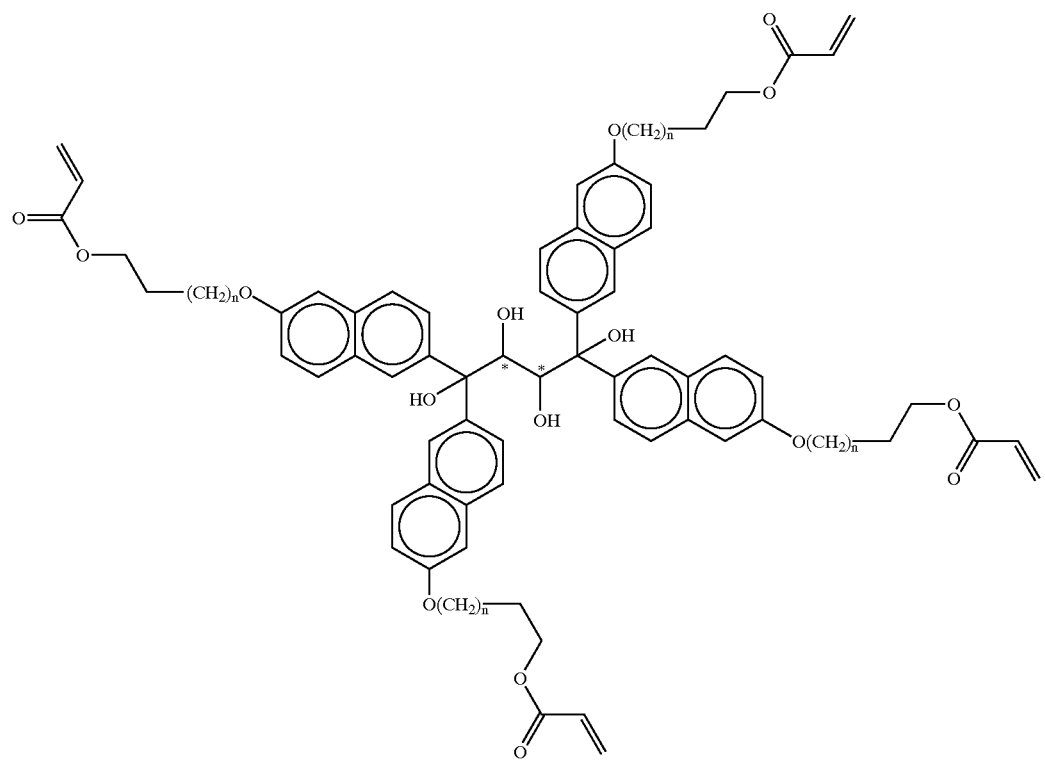

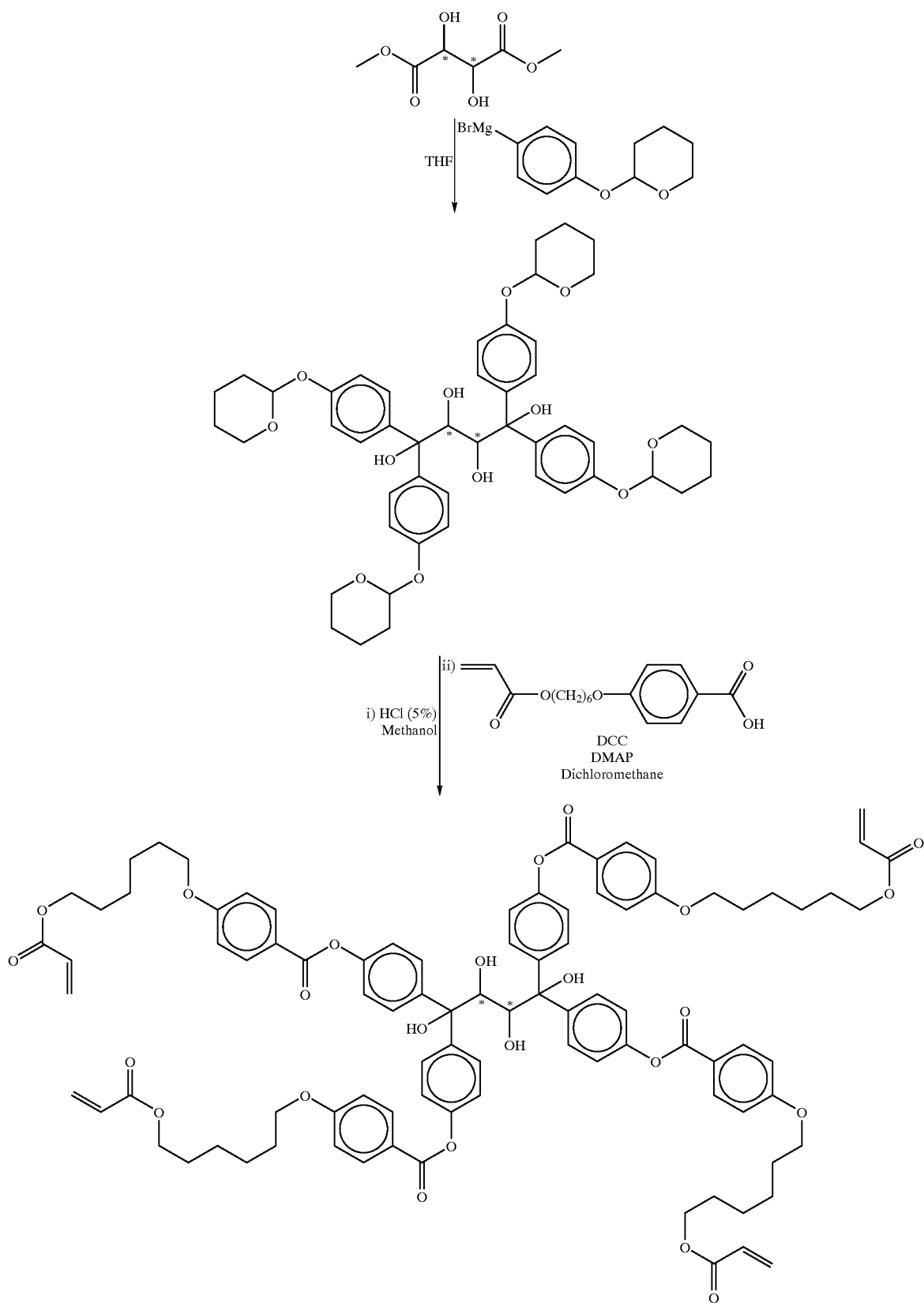
(Scheme 4)

Different methods can be used for the formation of the sought cholesteric network, starting from the polymerisable coloured cholesteric mixture manufactured as described above. Preferably, transparent substrates, optionally coated with ITO (indium tin oxide), and more preferably glass or plastic substrates, were used. Said substrates carried a layer of rubbed polyimide or polyamide or a layer of coated photopolymer. Said layers are used to orient the molecular helix which forms spontaneously in the cholesteric mixture. To preclude the formation of disclinations, the polymerisable cholesteric mixture was:

coated into a thin film, or provided between two of the said substrates which were sheared over a small distance until a planar order was obtained, or capillary filled between two of the said substrates, then subsequently cured, for example, by UV light, preferably in the presence of a photoinitiator, for example an IRGACURE™. Owing to the strength of the three-dimensional polymer network thus formed, the film may be peeled off and used, for example, as a self-supporting cholesteric polariser.

The reflected colour from the formed cholesteric layer is dependent on the pitch length of the cholesteric helix, said pitch length being itself dependent on the concentration of the optically-active dopant in, for example, a nematic host. For small and high concentrations of the optically-active dopant, the cholesteric network reflects red and blue colours respectively.

The novel optically active butane-1,2,3,4-tetraol derivatives of formula I are highly suitable for producing cholesteric films which can be used in different optical and electro-optical applications.

EXAMPLE 1

Preparation of (2R,3R)-1,1,4,4-tetranaphthalen-2-yl-butane-1,2,3,4-tetraol

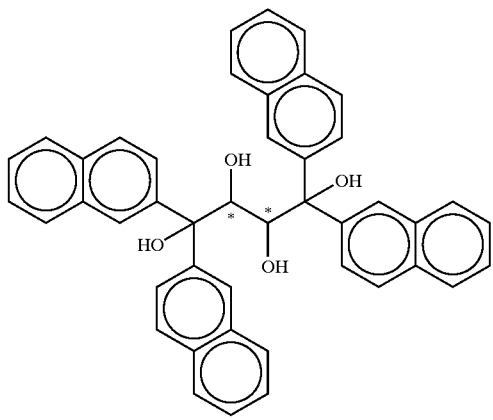

Under argon, 20.71 g of 2-bromonaphthalene are added to a suspension of magnesium (2.43 g) in 60 ml of dry THF. The obtained mixture is stirred for 2 h at room temperature (with occasional cooling within a ice bath, the reaction being exothermic). Then a solution of L-(+)-dimethyl tartrate (2.23 g) in 20 ml of dry THF is added dropwise to the cooled reaction mixture at 0° C. After complete addition (20 min), the reaction mixture is stirred for a further 4 h at room temperature, poured into saturated $NH_4Cl$ solution (150 ml) and extracted with ether (3×250 ml). The combined ether extracts are washed with saturated NaCl solution, dried over magnesium sulphate and evaporated to dryness. The obtained yellow-brown residue is chromatographed on silica gel ($CH_2Cl_2$, $CH_2Cl_2/Et_2O$: 9/1). This affords (2R,3R)-1,1,4,4-tetranaphthalen-2-ylbutane-1,2,3,4-tetraol as white crystalline material.

Yield: 6.2 g.

According to the procedure of Example 1, the following chiral 1,1,4,4-tetraarylbutane-1,2,3,4-tetraol derivatives are prepared:

(2R,3R)-1,1,4,4-Tetra-p-tolylbutane-1,2,3,4-tetraol

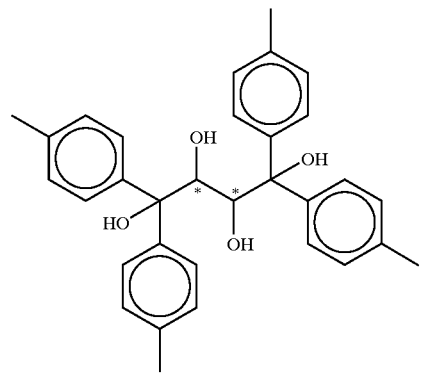

(2R,3R)-1,1,4,4-Tetracyclohexylbutane-1,2,3,4-tetraol

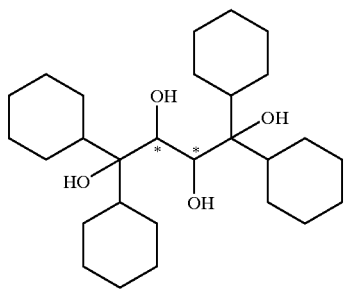

(2R,3R)-1,1,4,4-Tetrakis-[4-(tetrahydropyran-2-yloxy)phenyl]-butane-1,2,3,4-tetraol

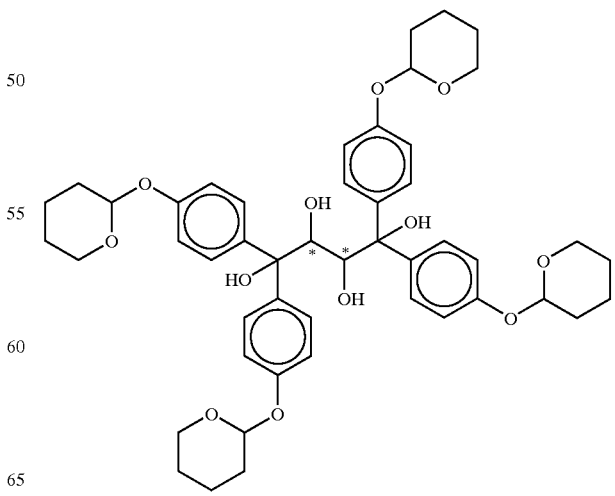

17
(2R,3R)-1,1,4,4-Tetranaphthalen-1-ylbutane-1,2,3,4-tetraol
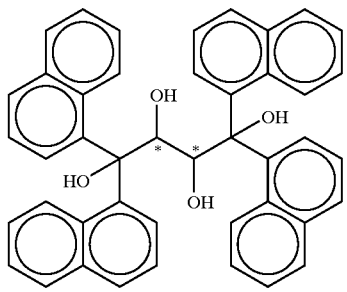
(2R,3R)-1,1,4,4-Tetranaphthalen-1-ylbutane-1,2,3,4-tetraol
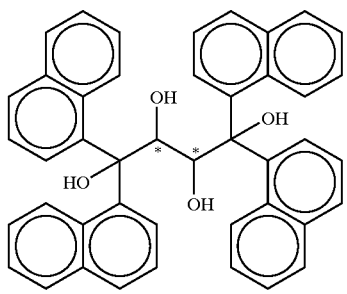
18
(2R,3R)-1,1,4,4-Tetranaphthalen-2-ylbutane-1,2,3,4-tetraol
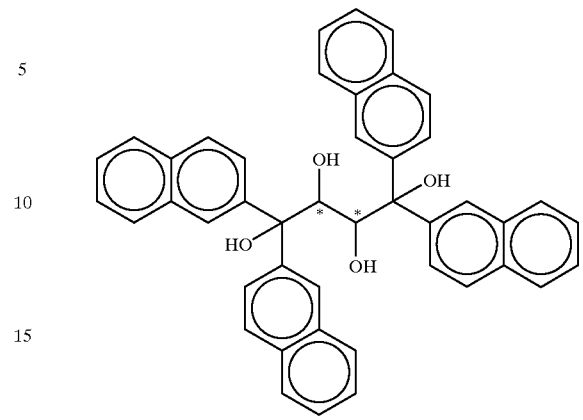
(2R,3R)-1,1,4,4-Tetrakisbiphenyl-4-ylbutane-1,2,3,4-tetraol
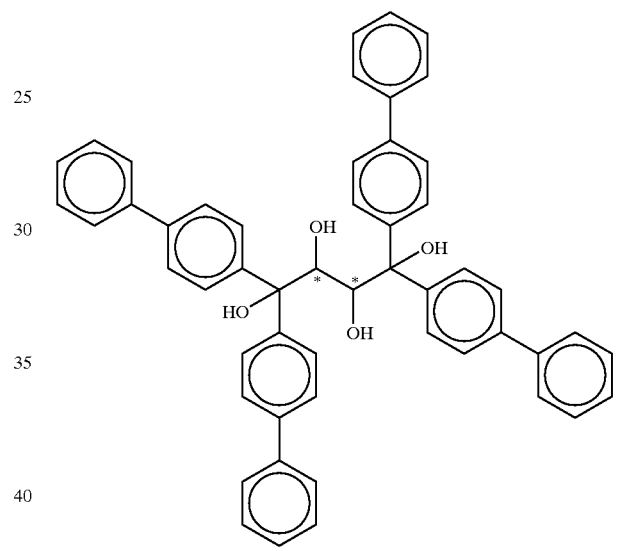
(2R,3R)-1,1,4,4-Tetrakis-(6-pent-4-enyloxynaphthalen-2-yl)-butane-1,2,3,4-tetraol
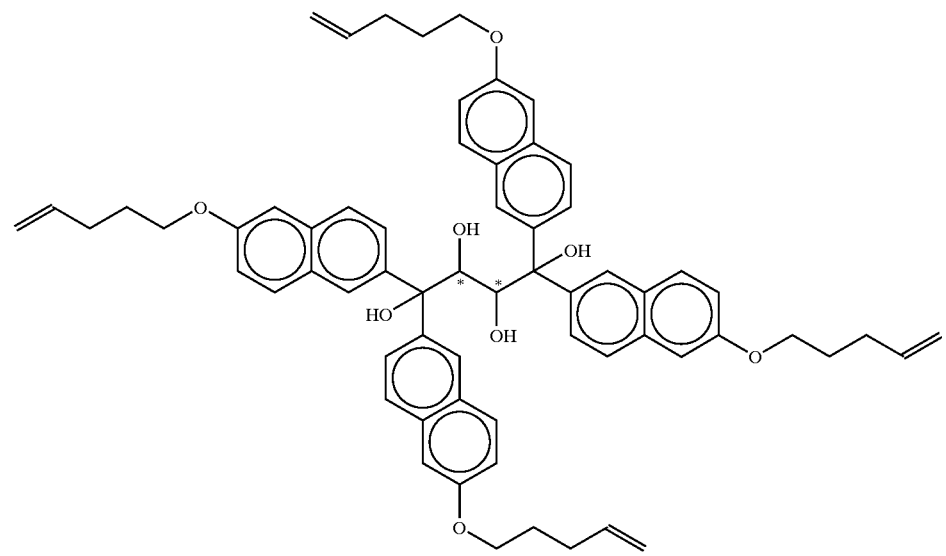

(2R,3R)-1,1,4,4-Tetraphenanthren-9-ylbutane-1,2,3,4-tetraol

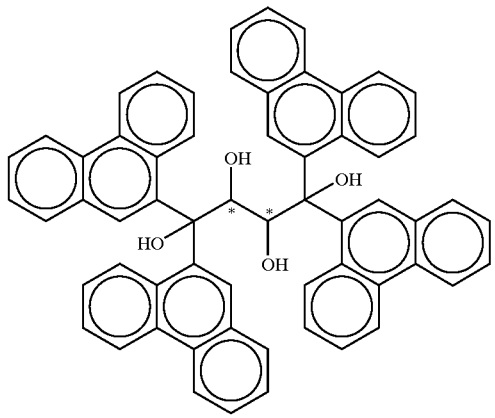

(4R,5R)-3,6-Diisopropyl-2,7-dimethyloctane-3,4,5,6-tetraol

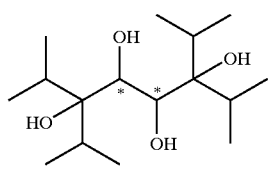

(4R,5R)-3,6-Di-tert-butyl-2,2,7,7-tetramethyloctane-3,4,5,6-tetraol

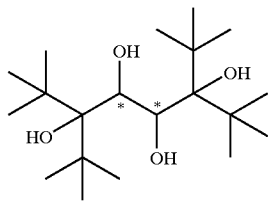

(11R,12R)-10,13-Dinonyldocosane-10,11,12,13-tetraol

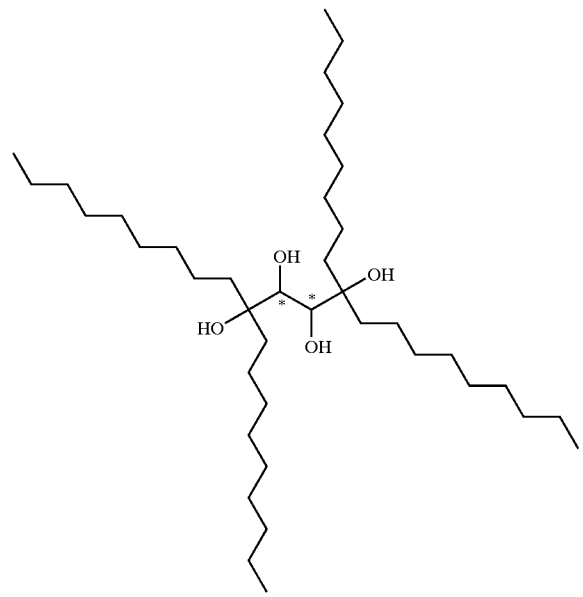

EXAMPLE 2

(2R,3R)-2,3-Bis-[4-(6-acryloyloxyhexyloxy)benzoyloxy]-1,1,4,4-tetranaphthalen-1-ylbutane-1,4-diol

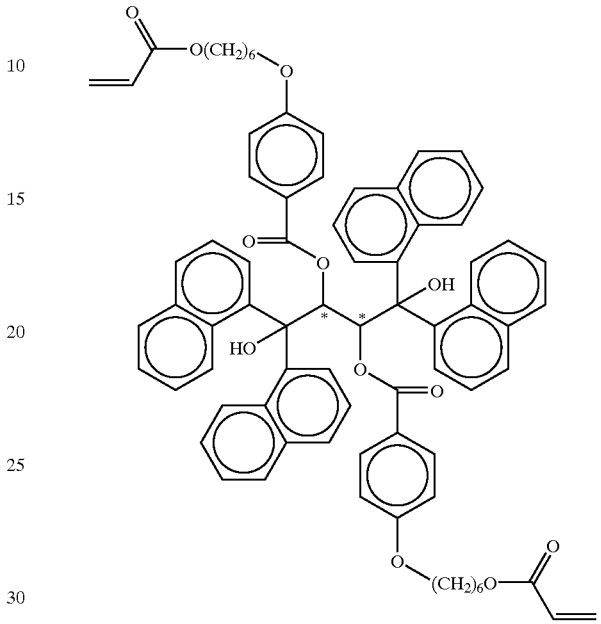

To a stirred solution of (2R,3R)-1,1,4,4-tetranaphthalen-1-ylbutane-1,2,3,4-tetraol (0.78 g), 4-(6-acryloyloxyhexyloxy)-benzoic acid (1.46 g) and 4-dimethylaminopyridine (DMAP) (0.61 g) in dichloromethane (20 ml), a solution of N,N'-dicyclohexylcarbodiimide (DCC) (1.03 g) in dichloromethane (10 ml) was added dropwise. After complete addition (15 min), the reaction mixture was further stirred for 48 h at room temperature. It was then filtered and the filtrate was concentrated under reduced pressure. The obtained oily residue was chromatographed on silica gel (CH$_2$Cl$_2$, CH$_2$Cl$_2$/Et$_2$O: 9/1) affording (2R,3R)-2,3-bis-[4-(6-acryloyloxyhexyloxy)benzoyloxy]-1,1,4,4-tetranaphthalen-1-ylbutane-1,4-diol as white crystalline material.

Yield: 0.56 g.

According to the procedure of Example 2, the following chiral polymerisable 1,1,4,4-tetraarylbutane-1,2,3,4-tetraol derivatives are prepared:

(2R,3R)-2,3-Bis-[4-(6-acryloyloxyhexyloxy)benzoyloxy]-1,1,4,4-tetranaphthalen-2-ylbutane-1,4-diol

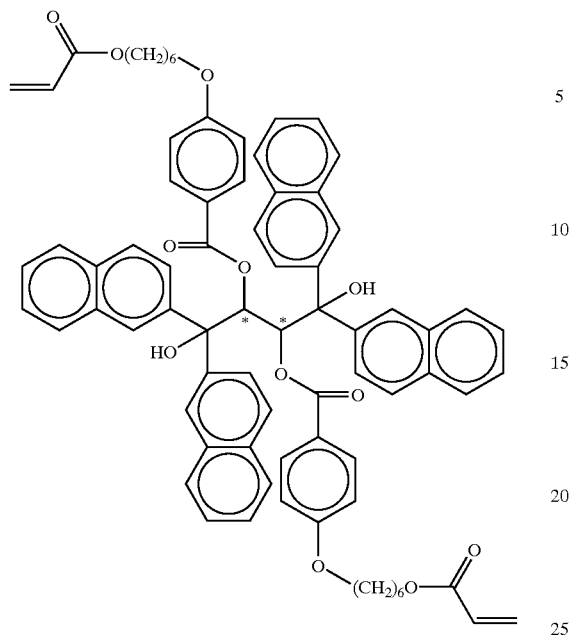
(2R,3R)-1,1,4,4-Tetrakis-[4-(6-acryloyloxyhexyloxy)benzoyloxyphenyl]butane-1,2,3,4-tetraol
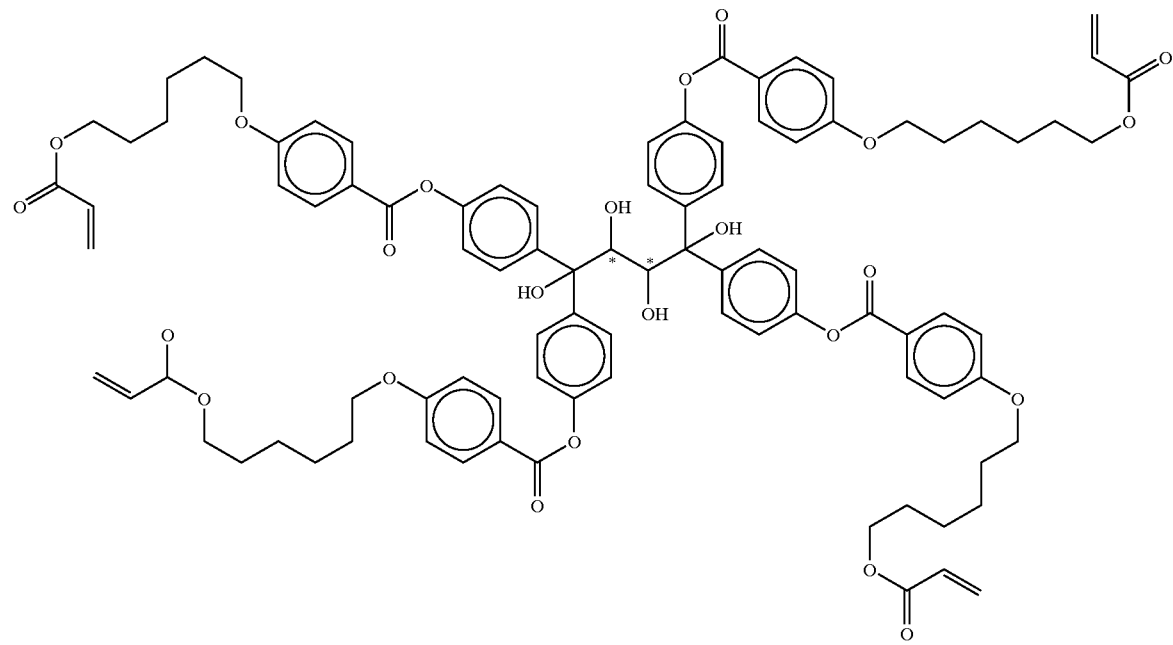

(2S,3S)-2,3-Bis-[4-(6-acryloyloxyhexyloxy)-benzoyloxy]-1,1,4,4-tetranaphthalen-2-ylbutane-1,4-diol
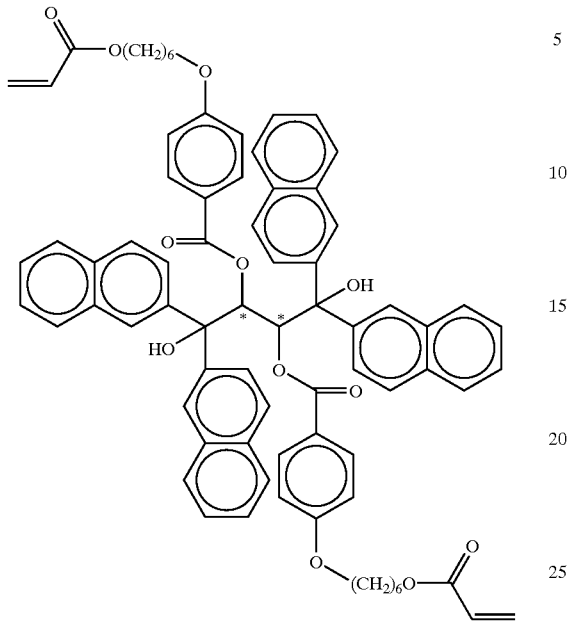
(2R,3R)-2,3-Bis-[4'-(6-acryloyloxyhexyloxy)biphenyl-4-carbonyloxy]-1,1,4,4-tetranaphthalen-2-ylbutane-1,4-diol
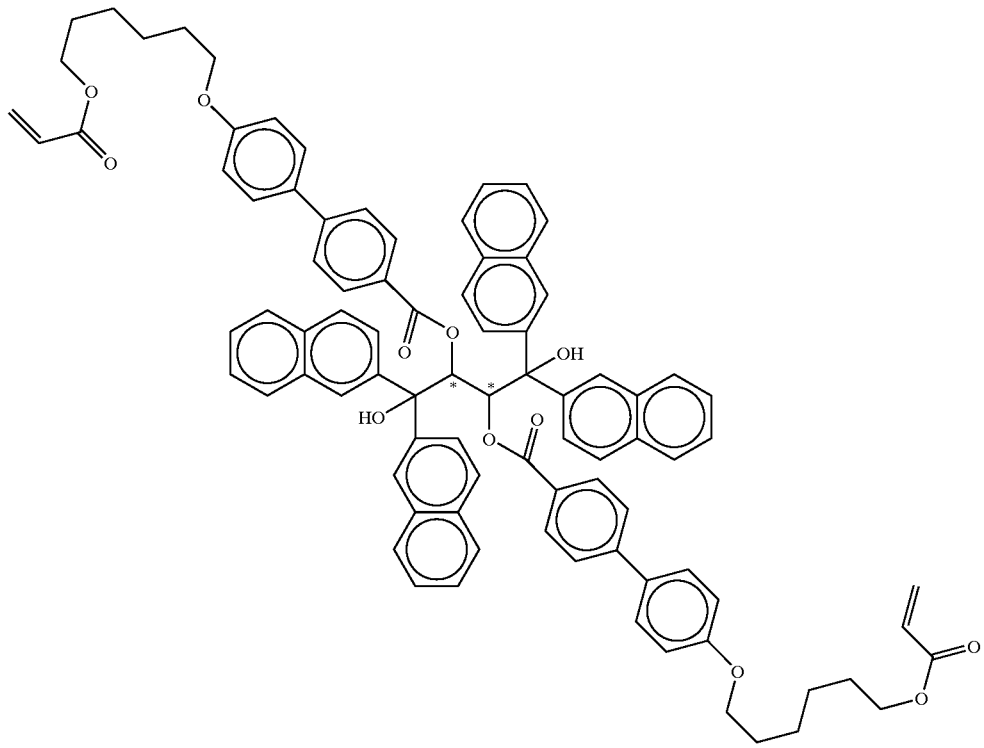

(2S,3S)-2,3-Bis-[4'-(6-acryloyloxyhexyloxy)biphenyl-4-carbonyloxy]-1,1,4,4-tetranaphthalen-2-ylbutane-1,4-diol
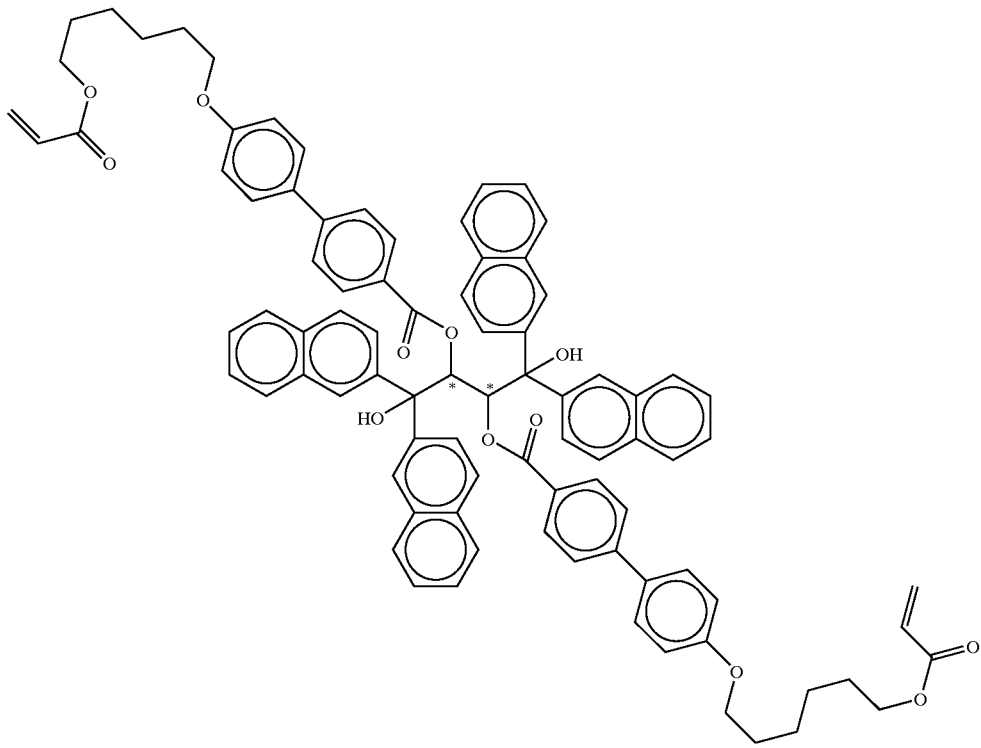
(11R,12R)-11,12-Bis-[4-(6-acryloyloxyhexyloxy)benzoyloxy]-10,13-dinonyldocosane-10,13-diol
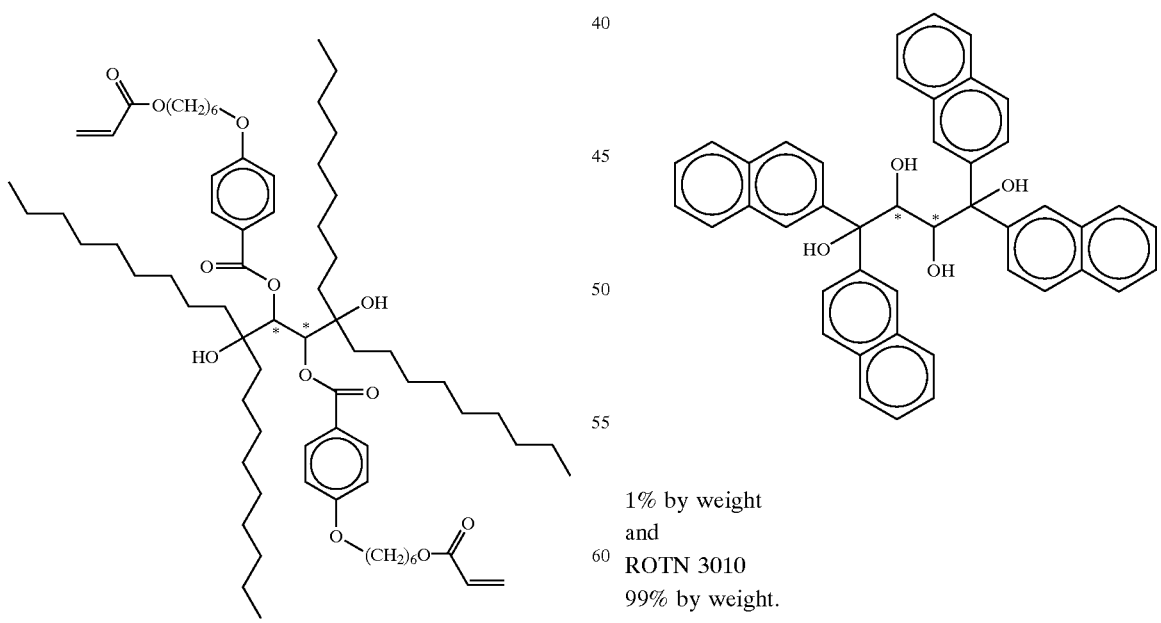
EXAMPLE 3
A mixture is formulated consisting of:
1% by weight
and
ROTN 3010
99% by weight.

The liquid crystal mixture ROTN 3010 is available from Rolic Research Ltd., Switzerland.

Forms a cholesteric phase with a pitch of p=2.25 μm.

EXAMPLE 4

A mixture is formulated consisting of:

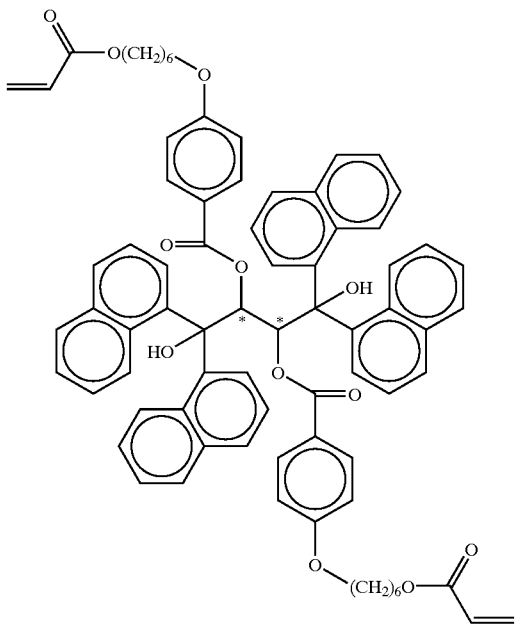

15% by weight
and

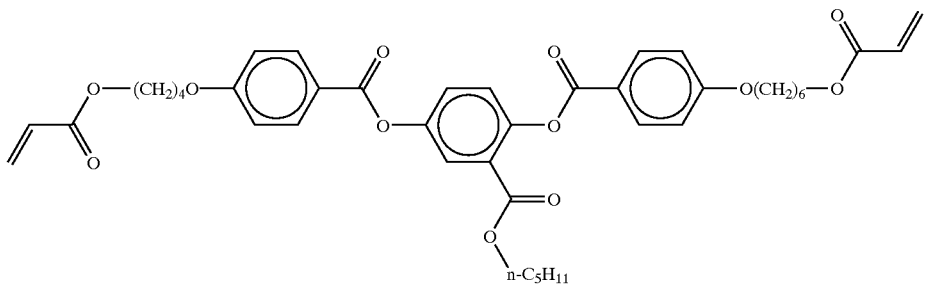

85% by weight

Forms a cholesteric phase with a pitch of p=370 nm.

What is claimed is:

1. An optically active butane-1,2,3,4-tetraol derivative of formula I:

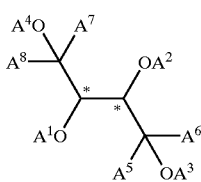

(I)

in which $A^1$, $A^2$, $A^3$, $A^4$ each independently represents hydrogen; or an optionally-substituted methyl group; or an optionally-substituted aliphatic group with 2 to 80 C-atoms, in which one or more C-atoms may be replaced by a heteroatom or a group —SO—, —SO$_2$—, —SOO—, —OSO— or —SOS—; or an optionally-substituted aromatic or non-aromatic carbocyclic or heterocyclic ring system, with 2 to 80 C-atoms; and $A^5$, $A^6$, $A^7$, $A^8$ each independently represents an optionally-substituted aliphatic group with 3 to 80 C-atoms, in which a C-atom, or two or more non-adjacent C-atoms, may be replaced by a heteroatom or a group —SO—, —SO$_2$—, —SOO—, —OSO— or —SOS—; or an optionally-substituted aromatic or non-aromatic carbocyclic or heterocyclic ring system, with 2 to 80 C-atoms; or one, two or three of $A^5$, $A^6$, $A^7$ and $A^8$ independently represents hydrogen; or an optionally-substituted methyl group; or an optionally-substituted aliphatic group with 2 C-atoms, in which a C-atom may be replaced by a heteroatom or a group —SO—, —SO$_2$—, —SOO—, —OSO— or —SOS—; and the remainder of $A^5$, $A^6$, $A^7$, $A^8$ independently represent an optionally-substituted aliphatic group with 3 to 80 C-atoms, in which a C-atom, or two or more non-adjacent C-atoms, may be replaced by a heteroatom or a group —SO—, —SO$_2$—, —SOO—, —OSO— or —SOS—; or an optionally-substituted aromatic or non-aromatic carbocyclic or heterocyclic ring system, with 2 to 80 C-atoms; with the provisos that:

when one, two or three of $A^5$, $A^6$, $A^7$ and $A^8$ represents hydrogen, then $A^5$, $A^6$, $A^7$ and $A^8$ may not represent COOH; and when $A^5$, $A^6$, $A^7$ and $A^8$ are all phenyl, then at least one of $A^1$, $A^2$, $A^3$, $A^4$ does not represent hydrogen.

2. An optically active butane-1,2,3,4-tetraol derivative as claimed in claim 1, wherein $A^5$, $A^6$, $A^7$ and $A^8$ each independently represents an optionally-substituted aliphatic group with 3 to 80 C-atoms, in which a C-atom, or two or more non-adjacent C-atoms, may be replaced by a heteroatom or a group —SO—, —SO$_2$—, —SOO—, —OSO— or —SOS—; or an optionally-substituted aromatic or non-aromatic carbocyclic or heterocyclic ring system, with 2 to 80 C-atoms.

3. An optically active butane-1,2,3,4-tetraol derivative as claimed in claim 1, wherein at least one of $A^1$ to $A^8$ includes a polymerizable group.

4. An optically active butane-1,2,3,4-tetraol derivative as claimed in claim 1, wherein:

$A^5$ to $A^8$ have each independently one of the meanings of formula II:

$$—X^1—(Sp^1)_n—X^2—(MG)—X^3—(Sp^2)_m—P \qquad (II);$$

A¹ to A⁴ are hydrogen atoms or have each independently one of the meanings of formula IIb or one of the meanings of formula IIc:

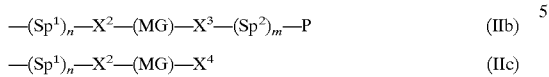

—(Sp¹)ₙ—X²—(MG)—X³—(Sp²)ₘ—P      (IIb)

—(Sp¹)ₙ—X²—(MG)—X⁴      (IIc)

in which:
X¹ to X³ each independently denote —O—, —S—, —NH—, —N(CH₃)—, —CH(OH)—, —CO—, —CH₂(CO)—, —SO—, —CH₂(SO)—, —SO₂—, —CH₂(SO₂)—, —COO—, —OCO—, —OCO—O—, —S—CO—, —CO—S—, —SOO—, —OSO—, —SOS—, —CH₂—CH₂—, —OCH₂—, —CH₂O—, —CH=CH—, —C≡C— or a single bond, in such a manner that oxygen atoms are not linked directly to one another;

X⁴ is a halogen;

Sp¹ and Sp² are each independently straight or branched spacer groups having 1 to 20 C-atoms which may be unsubstituted, or mono- or polysubstituted by halogen or CN, it being also possible for one or more non-adjacent CH₂ groups to be replaced, in each case independently from one another, by —O—, —S—, —NH—, —N(CH₃)—, —CH(OH)—, —CO—, —CH₂(CO)—, —CH₂(SO)—, —CH₂(SO₂)—, —COO—, —OCO—, —OCO—O—, —S—CO—, —CO—S—, —C≡C—, —(CF₂)ᵣ—, —(CD₂)ₛ— or —C(W¹)=C(W²)—, r and s ranging from 1 to 15, and W¹ and W² each independently denoting H, H—(CH₂)_q— or Cl with q ranging from 1 to 15;

P is hydrogen or a polymerisable group selected from the formulae CH₂=CW—, —CH₂=CW—COO—, CH₂=C(Ph)—COO—, CH₂=CH—COO—Ph—, CH₂=CW—CO—NH—, CH₂=C(Ph)—CONH—, CH₂=C(COOR')—CH₂—COO—, CH₂=CH—O—, CH₂=CH—OOC—, Ph—CH=CH—, CH₃—C=N—(CH₂)_m3—, HO—, HS—, HO—(CH₂)_m3—, HS—(CH₂)_m3—, HO(CH₂)_m3COO—, HS(CH₂)_m3COO—, HWN—, HOC(O)—, CH2=CH—Ph—(O)_m4,

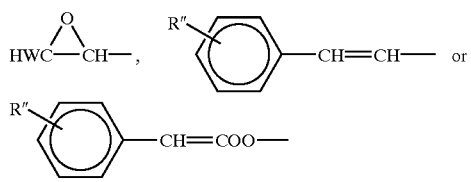

with W being H, Cl or alkyl with 1–5 C atoms, m3 being 1–9, m4 being 0 or 1, Ph being phenyl, R' being alkyl with 1–5 C atoms, and R" having the meaning of R' or being methoxy, cyano or a halogen;

n and m are each independently 0 or 1; and

MG is a mesogenic group consisting 1 to 4 aromatic or non-aromatic carbocyclic or heterocyclic ring systems and optionally up to 3 bridging groups.

5. An optionally active butane-1,2,3,4-tetraol derivative as claimed in claim 4, in which P is a polymerisable group.

6. An optically active butane-1,2,3,4-tetraol derivative as claimed in claim 4, in which MG is a group selected from the meanings of formula III:

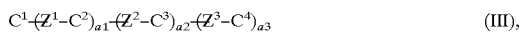

C¹—(Z¹-C²)_{a1}—(Z²-C³)_{a2}—(Z³-C⁴)_{a3}      (III), in which:
C¹ to C⁴ are in each case independently optionally-substituted non-aromatic, aromatic, carbocyclic or heterocyclic groups;

Z¹ to Z³ are independently from each other —COO—, —OCO—, —CH₂—CH₂—, —OCH₂—, —CH₂O—, —CH=CH—, —C≡C—, —CH=CH—COO—, —OCO—CH=CH— or a single bond; and a1, a2 and a3 are independently integers 0 to 3, such that a1+a2+a3≦4.

7. An optically active butane-1,2,3,4-tetraol derivative as claimed in claim 6, in which C¹ to C⁴ are selected from:

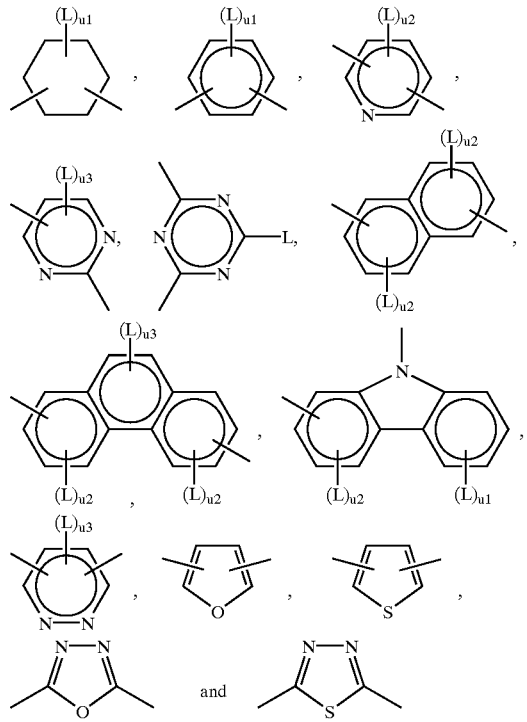

with:
L being —CH₃, —COCH₃, —NO₂, CN, or halogen,
u1 being 0, 1, 2, 3, or 4,
u2 being 0, 1, 2, or 3, and
u3 being 0, 1, or 2.

8. An optically active butane-1,2,3,4-tetraol derivative as claimed in claim 1, wherein:
A¹ and A² are identical, and
A³ and A⁴ are identical, and
A⁵–A⁸ are identical.

9. An optically active butane-1,2,3,4-tetraol derivative as claimed in claim 8, wherein:
A³ and A⁴ have one of the meanings of formula IV:

(Sp²)_{m4}—(O)_{m5}—P²      (IV)

A¹ and A² have one of the meanings of formula VA:

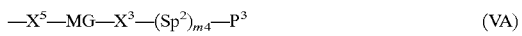

—X⁵—MG—X³—(Sp²)_{m4}—P³      (VA)

and $A^5$–$A^8$ have one of the meanings of formula VB:

$$—MG—X^3—(Sp^2)_{m_4}—P^3 \quad (VB)$$

in which:
$Sp^2$ is alkylene with 0 to 20 C-atoms;
$P^2$ is H, $CH_2=CW^5—$ or $CH_2=CW^5—CO—$;
$P^3$ is H, $CH_2=CW^5—$, $CH_2=CW^5—COO—$, $W^5CH=CH—O—$ or $CH_2=CW^5—O—$, with $W^5$ being H, $CH_3$, or Cl;
$m_4$ and $m_5$ are each independently 0 or 1 in such a manner that oxygen atoms are not linked directly to one another;
MG is selected from:

[structures with (L)$_{u1}$, (L)$_{u2}$, (L)$_{u3}$ substituents]

and $x^3$ is —O—, —CO—, —COO—, —OCO—, —CH$_2$—CH$_2$—, —OCH$_2$—, —CH$_2$O—, —CH=CH—, —C≡C—, —CH=CH—COO—, —OCO—CH=CH— or a single bond; and
$x^5$ is —CO— or —CH$_2$—; with
L being —CH$_3$, —COCH$_3$, —NO$_2$, CN, or halogen,
u1 being 0, 1, 2, 3, or 4,
u2 being 0, 1, 2, or 3, and
u3 being 0, 1, or 2.

10. An optically active butane-1,2,3,4-tetraol derivative as claimed in claim 9, in which:
MG is cyclohexylene, phenylene, biphenylene, naphthylene or phenanthrylene;
$X^3$ denotes —O—, —CO—, —COO—, —OCO—, —C≡C—, or a single bond, —O— or single bond;
$Sp^2$ is a straight-chain of formula —(CH$_2$)$_v$—, with v being an integer from 0 to 20;
$P^2$ is H, $CH_2=CW^5—$ or $CH_2=CW^5—CO—$;
$P^3$ is H, $CH_2=CW^5—$, $CH_2=CW^5—COO—$, $W^5CH=CH—O—$ or $CH_2=CW^5—O—$, with $W^5$ being H, $CH_3$, or Cl; and
$m^4$ and $m^5$ are each independently 0 or 1 in such a manner that oxygen atoms are not linked directly to one another.

11. An optically active butane-1,2,3,4-tetraol derivative as claimed in claim 10, in which $Sp^2$ is ethylene, propylene, butylene, pentylene, hexylene, heptylene, octylene, nonylene, decylene, undecylene, or dodecylene.

12. An optically active butan-1,2,3,4-tetraol derivative as claimed in claim 10, in which $X^3$ denotes —O— or a single bond.

13. A liquid crystalline mixture comprising at least one optically active butane-1,2,3,4-tetraol derivative of formula I according to claim 1.

14. A liquid crystalline mixture as claimed in claim 13, essentially consisting of:
i) at least one polymerisable non-optically-active liquid crystal,
ii) an optically active compound of formula I,
iii) a photoinitiator, and
iv) a stabiliser.

15. A process for making an optically-active liquid crystalline film, which comprises ordering the mixture as claimed in claim 14 in the monomeric state, and in situ UV polymerizing the ordered mixture.

16. An optically-active liquid crystalline film made by the process of claim 15.

17. An optically-active liquid crystalline film as claimed in claim 16, which is capable of selectively reflecting light of visible wavelengths.

18. A method for polarizing light, which comprises passing the light through an optically-active liquid crystalline film as claimed in claim 16.

19. A method for doping a liquid crystal, which comprises adding to the liquid crystal an effective amount of an optically active butane-1,2,3,4-tetraol derivative as claimed in claim 1.

20. A method for converting a liquid crystalline nematic phase to the cholesteric phase, which comprises adding to the liquid crystalline nematic phase an effective amount of an optically active butane-1,2,3,4-tetraol derivative as claimed in claim 1.

21. An optically active butane-1,2,3,4-tetraol derivative as claimed in claim 1, wherein optionally-substituted means unsubstituted or substituted with alkyl, aryl, cycloalkyl, amino, cyano, epoxy, halogen, hydroxy, nitro, or oxo.

22. An optically active butane-1,2,3,4-tetraol derivative as claimed in claim 1, wherein heteroatom means nitrogen, oxygen, or sulphur.

23. An optically active butane-1,2,3,4-tetraol derivative as claimed in claim 1, wherein optionally-substituted means unsubstituted or substituted with alkyl, aryl, cycloalkyl, amino, cyano, epoxy, halogen, hydroxy, nitro, or oxo; and wherein heteroatom means nitrogen, oxygen, or sulphur.

* * * * *